(12) United States Patent
Marshall et al.

(10) Patent No.: US 8,926,510 B2
(45) Date of Patent: Jan. 6, 2015

(54) DEVICE AND METHOD FOR GLAUCOMA MANAGEMENT AND TREATMENT

(75) Inventors: Andrew J. Marshall, Seattle, WA (US); Max G. Maginness, Seattle, WA (US); Michel Alvarez, Seattle, WA (US)

(73) Assignee: Istar Medical SA, Isnes (BE)

( * ) Notice: Subject to any disclaimer, the term of this patent is extended or adjusted under 35 U.S.C. 154(b) by 0 days.

(21) Appl. No.: 13/457,882

(22) Filed: Apr. 27, 2012

(65) Prior Publication Data

US 2012/0302861 A1 Nov. 29, 2012

(30) Foreign Application Priority Data

Apr. 27, 2011 (EP) ..................................... 11163979

(51) Int. Cl.
- *A61B 3/16* (2006.01)
- *A61B 5/00* (2006.01)
- *A61F 9/007* (2006.01)

(52) U.S. Cl.
CPC ................ *A61B 3/16* (2013.01); *A61B 5/0031* (2013.01); *A61F 9/00781* (2013.01)
USPC ............................ 600/398; 600/399; 600/561

(58) Field of Classification Search
USPC .................. 600/398–406, 561, 587
See application file for complete search history.

(56) References Cited

U.S. PATENT DOCUMENTS

| | | |
|---|---|---|
| 5,520,631 A | 5/1996 | Nordquist et al. |
| 5,704,907 A | 1/1998 | Nordquist et al. |
| 5,807,406 A * | 9/1998 | Brauker et al. ............... 424/423 |
| 5,882,327 A * | 3/1999 | Jacob ................................ 604/8 |
| 6,102,045 A | 8/2000 | Nordquist et al. |
| 6,579,235 B1 * | 6/2003 | Abita et al. .................... 600/398 |
| 6,616,699 B2 | 9/2003 | Zilla et al. |

(Continued)

FOREIGN PATENT DOCUMENTS

| | | |
|---|---|---|
| EP | 1 670 385 B1 | 1/2013 |
| EP | 2 517 619 B1 | 5/2013 |

(Continued)

OTHER PUBLICATIONS

Chen et al., "Wireless Intraocular Pressure Sensing Using Microfabricated Minimally Invasive Flexible-Coiled LC Sensor Implant," *Journal of Microelectromechanical Systems* 19(4): 721-734, Aug. 2010.

(Continued)

*Primary Examiner* — Devin Henson
(74) *Attorney, Agent, or Firm* — Seed IP Law Group PLLC (57) ABSTRACT

Described herein is a device for glaucoma treatment and monitoring that comprises a combination of an intraocular pressure (IOP) sensor and a glaucoma drainage device. The device comprises an IOP sensor and an inductive antenna mounted within a porous biocompatible material that forms the drainage path. The IOP sensor is mounted in a footplate portion of the device and is mountable in the anterior chamber of an eye. The footplate portion is connected to a body portion that houses the spiral antenna by a neck portion which retains the footplate portion in a suitable position within the anterior chamber. Due to its size, the footplate portion housing the IOP sensor can readily be inserted into the anterior chamber with the body portion housing the spiral antenna located outside of the anterior chamber in a sub-scleral space to disperse the aqueous humour.

35 Claims, 4 Drawing Sheets

(56) References Cited

U.S. PATENT DOCUMENTS

| | | | |
|---|---|---|---|
| 6,699,210 B2 * | 3/2004 | Williams et al. | 604/8 |
| 6,939,299 B1 * | 9/2005 | Petersen et al. | 600/398 |
| 7,037,335 B2 * | 5/2006 | Freeman et al. | 623/4.1 |
| 7,160,264 B2 | 1/2007 | Lisk, Jr. et al. | |
| 7,207,965 B2 | 4/2007 | Simon | |
| 7,220,238 B2 | 5/2007 | Lynch et al. | |
| 7,431,709 B2 | 10/2008 | Pinchuk et al. | |
| 7,594,899 B2 | 9/2009 | Pinchuk et al. | |
| 7,677,107 B2 | 3/2010 | Nunez et al. | |
| 7,678,065 B2 | 3/2010 | Haffner et al. | |
| 7,837,644 B2 | 11/2010 | Pinchuk et al. | |
| 7,972,628 B2 * | 7/2011 | Ratner et al. | 424/499 |
| 8,007,459 B2 | 8/2011 | Haffner et al. | |
| 8,152,752 B2 | 4/2012 | Lynch et al. | |
| 8,257,295 B2 * | 9/2012 | Rickard et al. | 604/9 |
| 8,318,193 B2 | 11/2012 | Ratner et al. | |
| 8,372,423 B2 | 2/2013 | Marshall et al. | |
| 8,388,568 B2 | 3/2013 | Lynch et al. | |
| 8,444,588 B2 | 5/2013 | Yablonski | |
| 8,475,374 B2 | 7/2013 | Irazoqui et al. | |
| 2003/0055372 A1 * | 3/2003 | Lynch et al. | 604/8 |
| 2006/0136071 A1 | 6/2006 | Maspero et al. | |
| 2008/0228127 A1 | 9/2008 | Burns et al. | |
| 2009/0069648 A1 * | 3/2009 | Irazoqui et al. | 600/302 |
| 2009/0275924 A1 | 11/2009 | Lattanzio et al. | |
| 2009/0299216 A1 | 12/2009 | Chen et al. | |
| 2010/0152641 A1 | 6/2010 | Yablonski | |
| 2010/0168644 A1 | 7/2010 | Brown | |
| 2010/0249691 A1 | 9/2010 | Van Der Mooren et al. | |
| 2011/0071456 A1 | 3/2011 | Rickard | |
| 2011/0082385 A1 | 4/2011 | Diaz et al. | |
| 2011/0098629 A1 | 4/2011 | Juan, Jr. et al. | |
| 2011/0196281 A1 | 8/2011 | Lynch et al. | |
| 2012/0184892 A1 | 7/2012 | Bigler et al. | |
| 2012/0220917 A1 | 8/2012 | Silvestrini et al. | |
| 2012/0302861 A1 | 11/2012 | Marshall et al. | |
| 2012/0310137 A1 | 12/2012 | Silvestrini | |
| 2013/0022648 A1 | 1/2013 | Maginness et al. | |

FOREIGN PATENT DOCUMENTS

| | | |
|---|---|---|
| WO | 03/093196 A1 | 11/2003 |
| WO | 2005/032418 A2 | 4/2005 |
| WO | 2011/127395 A1 | 10/2011 |

OTHER PUBLICATIONS

Kakaday et al., "Design of a Wireless Intraocular Pressure Monitoring System for a Glaucoma Drainage Implant," *ICBME 2008, Proceedings 23*: 198-201, 2009.

Kim et al., "Comparison of Glaucoma Drainage Implants: M4 vs FP7 and S2," *J. Glaucoma*, May 17, 2013, 3 pages.

Lim et al., "Glaucoma drainage devices; past, present, and future," *Br. J. Opthalmol 82*: 1083-1089, 1998. (8 pages).

Marshall et al., "Sphere Templated Angiogenic Regeneration (STAR) Biomaterials for Ophthalmic Applications," 2010, 1 page.

Marshall et al., "Quantitative Characterization of Sphere-Templated Porous Biomaterials," *AIChE Journal 51*(4): 1221-1232, 2005. (12 pages).

Oatts et al., "In Vitro and In Vivo Comparison of Two Suprachoroidal Shunts," *Invest Ophthmol Vis Sci 54*: 5416-5423, 2013. (8 pages).

* cited by examiner

DEVICE AND METHOD FOR GLAUCOMA MANAGEMENT AND TREATMENT

BACKGROUND

1. Technical Field

The present invention relates to improvements in or relating to glaucoma management and treatment, and is more particularly concerned with glaucoma devices that integrate both intraocular pressure sensors and glaucoma drainage devices.

2. Description of the Related Art

The mammalian eye comprises an anterior chamber located between the cornea and the iris and lens. This chamber is filled with a fluid known as aqueous humour. A trabecular meshwork, comprising a plurality of microscopic passageways, is located in the angle between the iris and the cornea. In the normal human eye, aqueous humour is generated at a constant rate, typically about 2.7 microliters per minute (µl/min), by the ciliary body behind the iris. This aqueous humour flows past the lens and iris and then exits via the trabecular meshwork and is returned to the circulatory system.

The intraocular pressure (IOP) maintaining this flow in the normal eye tends to remain within a range of 10 mmHg to 20 mmHg. However, there may be significant changes in the IOP related to the cardiac cycle, blinking, diurnally and other causes. This makes it difficult to obtain representative values of the IOP from infrequent measurements. In the most prevalent chronic form of glaucoma where the iris-cornea angle remains open, there is blockage of the trabecular meshwork fluid outflow path which causes a build-up of excess fluid in the eye, and, consequently raises IOP to a value consistently greater than about 18 mmHg. In some cases, the IOP may be as high as 50 mmHg or more. Over time, this pressure increase results in irreversible damage to the optic nerve and loss of vision.

Glaucoma is a major cause of blindness worldwide and affects over 60 million people. Glaucoma is associated with many conditions including high blood pressure, diabetes, steroid use and ethnic origins. Various treatments are currently available for glaucoma including drug regimes, laser trabeculoplasty, trabeculotomy and trabeculectomy and intraocular drainage implants.

Drugs are frequently administered in the form of eye drops to control fluid inflow, that is, the formation of aqueous humour, or to open the trabecular meshwork. Erratic dosages, side effects and poor patient compliance are common issues.

In an alternative to drug use for glaucoma treatment, surgical creation of shunt paths or drains around or through the meshwork blockage is adopted as a means to release excess fluid and hence the build-up of IOP. In trabeculoplasty, a laser is used to create small openings in the trabecular meshwork of the eye so that aqueous humour can drain through the meshwork to reduce the intraocular pressure in the anterior chamber of the eye. This method of treatment is mainly used for open angle glaucoma.

Surgical techniques include trabeculotomy and trabeculectomy. Trabeculotomy is a surgical technique in which an opening is created in the trabecular meshwork using a small instrument to allow the fluid to flow from the anterior chamber. Trabeculectomy is the most common surgical technique for glaucoma in which part of the trabecular meshwork is removed. These methods allow fluid to collect under the conjunctiva and be reabsorbed by the eye.

Implanted devices are most often used where other treatment methods have become ineffective, but, more recently, have been proposed as first choice, alone or in conjunction with drug therapy. These implants comprise drainage devices that are inserted into the eye so that aqueous humour can be drawn through a drainage path and away from the anterior chamber. In the most commonly used implants, for example, Molteno implants and Baerveldt shunts, a drain path is formed by a tube placed between the anterior chamber and a fluid dispersion plate located usually supra-sclerally, below the conjunctiva. Dispersed fluid from the plate forms a pool or "bleb" that is gradually re-absorbed into the outer layers of the eye.

However, the drainage plates of such devices may often be large and rigid, causing fibrotic reactions with the surrounding tissue that can progressively reduce effectiveness. For example, plates may have areas as large as 425 mm$^2$ and cover almost 25% of the surface area of the eye. Whilst dispersion plates can be curved to match the general shape of the external layers of the eye, these can only approximate to the actual shape of the eye of an individual patient. Mismatches in plate to sclera geometry can cause chronic microtrauma problems. Whilst more recent drain devices are of smaller size they are still rigid with the potential for trauma during insertion and in subsequent use.

By way of overcoming certain of these shortcomings, U.S. Pat. No. 6,102,045 describes a soft compact implant, with reduced fibrotic reaction, that lowers the intraocular pressure (IOP) in the eye. The implant, comprising a porous cellulosic membrane, extends into the anterior chamber of the eye, then through an opening in the limbus cornea to a drainage area underneath a scleral flap, and, preferably located between the sclera and choroid. Once implanted, fluid is absorbed from the drainage area into the choroidal vascular bed, enabling aqueous humour to be drained from the anterior chamber. Such soft devices, providing a drain or wick function, are often referred to as setons.

In detection and monitoring of glaucoma, routine ophthalmic examinations conducted on a yearly or other basis commonly include a measurement of IOP. However, this low frequency of measurement may fail to detect elevated pressure in a timely manner. Furthermore, a single measurement gives no indication of potentially damaging variations from day to day. The established "gold standard" tonometry instruments used require medical skill and are suited only for occasional use.

Several devices have been disclosed to more frequently measure IOP. In particular, certain of these use a pressure sensor surgically implanted within the eye, combined with external wireless, magnetic, optical or other means to interrogate the implant and obtain IOP readings.

It is most usual to deploy passive sensors, that is, sensors that do not need an internal power source, to avoid any battery chemicals in the eye. The interrogation methods then provide some externally applied form of energy to activate the implant when a reading is to be taken. The techniques often resemble those well understood in the radio frequency identification (RFID) field.

However, such sensors have the common limitation of requiring surgery specifically to implant them. In many cases, there may not be a medical risk-benefit justification for a surgical procedure. Therefore, IOP sensors combined with other ophthalmic devices, most commonly intraocular lenses (IOL), are utilised to avoid the need for additional surgery.

Many known IOP sensors are relatively large in the context of the eye dimensions and are necessarily rigid to obtain correct sensor and readout function. This risks optical path blockage and trauma. IOP sensors are described in U.S. Pat.

No. 7,677,107, U.S. Pat. No. 6,939,299, U.S. Pat. No. 6,579,235, US-A-2009/0299216 and US-A-2009/0069648.

U.S. Pat. No. 7,677,107 describes a wireless pressure sensor that comprises an inductor-capacitor arrangement sandwiched between protective layers of impermeable polymeric materials. The portion of a first substrate is configured to form a cavity with a first capacitor plate, an inductor also being formed on the first substrate. A second substrate having a second capacitor plate formed thereon is attached to the first substrate and seals the cavity formed in the first substrate, the second substrate being movable with respect to the first substrate. Changes in pressure are detected by corresponding capacitance variations resulting in changes to the resonant frequency of the combination. The inductor element is necessarily held rigid to maintain a stable value and cannot be conformal to the individual patient anatomy.

U.S. Pat. No. 6,939,299 describes a micromachined chip on which an inductor-capacitor arrangement is mounted. The capacitor comprises an upper plate and a lower plate that are prepositioned during fabrication. Changes in fluid pressure in the eye are cause plate deflections and thus capacitance changes, detectable as a change of resonant frequency in a similar manner to U.S. Pat. No. 7,677,107.

U.S. Pat. No. 6,579,235 describes a passive intraocular pressure sensor that operates with a monitoring recorder that is worn by the patient in whose eye the sensor is implanted. Magnetic coupling provides a link between the sensor and the monitoring device.

US-A-2009/0299216 describes an intraocular pressure sensor that uses a capacitor and a reference chamber to carry out pressure comparisons within the eye. The reference chamber has a predetermined acceptable pressure that is compared with the sensed pressure to provide an output indicative of the pressure within the eye.

US-A-2009/0069648 describes a microlectromechanical system (MEMS) device that uses piezo-resistive elements for sensing changes in pressure.

An intraocular pressure sensor is also described in an article entitled "Wireless Intraocular Pressure Sensing Using Microfabricated Minimally Invasive Flexible-Coiled LC Sensor Implant" by Po-Jui Chen, Saloomeh Saati, Rohit Varma, Mark S. Humayun and Yu-Chong Tai, Journal of Microelectromechanical Systems, Vol. 19, No. 4 Aug. 2010. In this article, passive wireless sensing is described using an implanted wireless pressure sensor comprising an electrical LC circuit with resonant frequency varying under pressure. The sensor includes a bendable coil substrate that can be folded for implant and expanded once implanted, resuming a rigid shape. Inductive coupling is used for a wireless link between the implanted sensor and an external device.

Once glaucoma has progressed to a stage where a drainage device has become medically indicated, the need and benefit for continuous IOP monitoring is self apparent. It is therefore advantageous to combine the insertion of a glaucoma drainage device with a pressure sensor. This requires only one surgical procedure for inserting both devices and provides a glaucoma management system that can readily be monitored.

Such a combination is described in U.S. Pat. No. 7,678,065. In U.S. Pat. No. 7,678,065, an IOP sensor is implanted at the same time as a drainage device. However, the sensor is not integral with the drainage device and after insertion must be separately attached within the eye, making the complexity comparable to two separate procedures.

In an article entitled "Design of a Wireless Intraocular Pressure Monitoring System for a Glaucoma Drainage Implant" by Kakaday T, Plunkett M, McInness S, Li J S, Voelker N H, Craig J E, Proc ICEMB 23, pages 198 to 201, 2009, a IOP sensor implant is described that is attached to the external plate of a Molteno glaucoma drainage device. The IOP sensor consists of a MEMS capacitive pressure sensor and a planar inductor printed directly onto a flexible, biocompatible polyimide printed circuit board (PCB) to complete a parallel resonant circuit, the circuit frequency varying with pressure and being externally detectable. The sensor implant is encapsulated in a biomaterial, polydimethylsiloxane (PDMS—commonly referred to as silicone rubber), to protect against the aqueous environment. The IOP sensor relies on the plate holding a generally fixed shape with predictable deflection under the pressure of fluid entering the plate via the tube from the anterior chamber. Disadvantages with such an implant include the added thickness of the drainage plate which can acerbate blistering effects occurring from bleb formation, and the measurement is of pressure in the drain plate rather than direct measurement of the pressure in the anterior chamber.

Whilst IOP sensors and drainage devices are known as discussed above, these devices are separate and tend to be located in different portions of the eye because of their different functions.

BRIEF SUMMARY

One embodiment provides an integrated intraocular pressure sensor and glaucoma drain device that requires a single surgical procedure for implantation, is conformable to eye anatomy and which is located in the eye at a position that is suitable for both pressure measurement and for providing drainage.

In accordance with a first embodiment of the present invention, there is provided an integrated intraocular device comprising: an intraocular pressure sensor element; an antenna element; and an aqueous humour drainage element; wherein the drainage element comprises a highly flexible, porous biocompatible material encasing the intraocular pressure sensor element and the antenna element.

Preferably, the drainage element comprises a body portion housing the antenna element and a footplate portion housing the intraocular pressure sensor element. The body portion and the footplate portion are connected to one another by a smaller section neck portion that is placed through a limbal incision during surgery to position the drainage device.

In one embodiment, the body portion is substantially circular and the antenna element comprises a circular spiral located within the circular body portion. In another embodiment, the body portion is substantially rectangular and the antenna element comprises a rectangular spiral located within the rectangular body portion. In each case, the antenna element may substantially be arranged around the periphery of the body portion.

The antenna element and the intraocular pressure sensor element are preferably connected by leads that pass between the body portion and the footplate portion. At least one protective layer may be located between the intraocular pressure sensor element, the antenna element, the leads and the porous biocompatible material, the porous biocompatible material encasing each protective layer.

Preferably, a single protective layer is formed around the intraocular pressure sensor element, the antenna element and the leads, the single protective layer having an opening in the vicinity of the intraocular pressure sensor element to allow pressure of the aqueous humour to be measured through the porous biocompatible material.

The porous biocompatible material may comprise a natural polymer or a synthetic polymer. In a preferred embodiment of the present invention, the synthetic polymer comprises silicone rubber.

The mean thickness of the porous biocompatible material is between 100 μm and 1000 μm, preferably, between 100 μm and 500 μm, more preferably, between 200 μm and 500 μm.

The porous biocompatible material comprises substantially spherical open pores having a mean pore diameter between 20 μm and 90 μm, preferably between 25 μm and 70 μm, and more preferably, between 25 μm and 30 μm. In the integrated intraocular device of the present invention, the preferred range is between about 25 μm and 30 μm.

The substantially spherical open pores may have pore interconnections between 15% and 40% of the mean pore diameter. Most often, there will be between 4 and 7 interconnections between any pore and its neighbours.

In one embodiment, the porous biocompatible material comprises an irregular outer surface having a "peaks and valleys" topography. The surface variations of the irregular outer surface may be between 100 μm and 300 μm about the mean thickness of the porous biocompatible material. By having this "peaks and valleys" topography in contact with the eye tissue when the device is implanted in the eye, fibrotic reactions to the implanted device can be further reduced. U.S. Published Application No. 2011/0257623 provides more detailed description of the "peaks and valleys" topography, which application is incorporated herein by reference in its entirety.

The porous biocompatible material provides a drain for aqueous humour flow with a resistance preferably not exceeding 1 mmHg pressure drop for a flow of 1 μl/min.

It is preferred that the antenna element comprises an inductive antenna element. The antenna element may be flexible and this provides an advantage that the device can readily conform to the eye contours after implantation, thus minimising trauma.

Preferably, the antenna element and the intraocular pressure sensor element are both passive.

The integrated intraocular device of the present invention further comprises an intraocular pressure sensor processing system, the intraocular pressure sensor itself forming a part of the said system. The intraocular pressure sensor processing system comprises a decoder for decoding interrogation signals received by the antenna element and a detector for obtaining power signals from these received signals. The processing system further comprises an energy storage module for operating power. In addition, the said system further comprises an encoder for encoding pressure readout signals to be transmitted by the antenna element.

In accordance with another aspect of the present invention, there is provided an intraocular pressure monitoring system comprising: an extracorporeal interrogation and processing system; an implanted integrated intraocular device as described above, the intraocular device being arranged to communicate wirelessly with the interrogation and processing system.

The interrogation and processing system preferably comprises a transceiver element for transmitting activation signals to the integrated intraocular device and for receiving signals corresponding to intraocular pressure measurements taken by the integrated intraocular device when activated. The interrogation and processing system may comprise a communications module for transmitting data relating to the intraocular pressure measurements to a remote location. The interrogation and processing system may be mounted in at least one of a pair of eye glasses, a wand, a pillowcase or a sheet, the pillowcase or sheet being suitable for receiving measurements when the patient is asleep. It will be appreciated that the interrogation and processing system may be split into component parts so that the transceiver can be located in a sheet that can be positioned under a pillow (or the pillowcase itself), the transceiver being connected to the rest of the interrogation and processing system by a cable. This means that transceiver can be removed from the sheet when the sheet is to be cleaned without damaging the system.

In accordance with a further aspect of the present invention, there is provided a method of monitoring intraocular pressure, the method comprising the steps of: (a) implanting an integrated intraocular device as described above; and (b) determining intraocular pressure measurements using the intraocular pressure sensor element within the integrated intraocular device; wherein step (a) comprises implanting the portion of the device having the intraocular pressure sensor element within the anterior chamber of the eye.

Step (a) comprises the steps of making a limbal incision in the eye; positioning the footplate portion within the anterior chamber of the eye, the neck portion being located in the limbal incision; and positioning the body portion within the exterior layers of the eye. Additionally, step (a) further comprises positioning the body portion between the choroid and the sclera of the eye.

Step (b) comprises using an extracorporeal device to interface with the intraocular pressure sensor element to obtain an output of the intraocular pressure measurements.

The present invention includes a glaucoma management system comprising a glaucoma drain device formed from an anatomically conformal porous biomaterial seton surgically implanted to form a fluid conducting path between the anterior chamber of the eye and the sclera, the seton comprising means for the measurement of intraocular pressure and other physiological conditions. A wireless readout is provided of such measurements using an external interrogation device adapted to provide energy to the implant and wirelessly obtain physiological measurement readouts.

In this way, a compact, fully integrated drain and sensor device can be implanted as a single device in a single procedure. Moreover, the sensor element can be correctly positioned to measure IOP directly in the anterior chamber while the drain extends from the anterior chamber to a sub-scleral region of the eye. Alternatively, if the drainage device has a low flow resistance, that is, less than about 1 mmHg pressure drop at a flow rate up to that of the natural input rate into the eye i.e., between about 1 and 3 μl/min, the pressure sensing element may be located in the diffusion area. Such alternative placement will depend on low flow resistance through the device, and the ability of the fluid to diffuse in any direction within, and consequently around, the drainage body. The porous biomaterial from which the integrated device of the present invention is made provides fluid pathways through its structure that are substantially the same in any direction. This provides an important condition for a pressure measurement at any one location to accurately represent the pressure of the larger eye volume.

In addition, the porous biomaterial structure provides control of fibrosis so that isotropic, low resistance flow paths are maintained through the material and pressure sensitivity changes with time are minimised.

Moreover, a device that is highly flexible is provided that allows self-contouring to the eye of each individual patient in which the device is implanted.

In addition to pressure measurement, additional sensors may be provided to measure further physiological conditions, for example, temperature, salinity of the aqueous humour, glucose concentration, the concentration of drugs topically applied to the eye.

BRIEF DESCRIPTION OF THE SEVERAL VIEWS OF THE DRAWINGS

For a better understanding of the present invention, reference will now be made, by way of example only, to the accompanying drawings in which.

DETAILED DESCRIPTION

The present invention will be described with respect to particular embodiments and with reference to certain drawings but the invention is not limited thereto. The drawings described are only schematic and are non-limiting. In the drawings, the size of some of the elements may be exaggerated and not drawn on scale for illustrative purposes.

In accordance with the present invention, an integrated IOP sensor and glaucoma drainage device is provided that comprises an IOP sensor element and an inductive antenna element. The IOP sensor element and the antenna element are sandwiched between at least two layers of an open pore biocompatible material. The biocompatible material has two functions, namely, to protect the sensor element and antenna from fibrotic encapsulation, and to form the drainage device. When the device is implanted the biocompatible open pore structure further allows communication of aqueous humour with the IOP sensor element within the integrated device.

A suitable biocompatible material structure is described in U.S. Pat. No. 7,792,628, which is incorporated herein by reference in its entirety. The described biocompatible material is porous and comprises a biocompatible polymer scaffold that defines an array of interconnected pores having similar diameters. The term "similar diameters" means that the difference in diameter between two pores is less than 20% of the larger diameter. Typically, the mean diameter of the pores is between about 20 µm and about 90 µm, preferably between about 25 µm and about 75 µm. For use in the integrated device of the present invention, the preferred range is between about 25 µm and about 30 µm.

Each pore is connected to at least 4 other pores by connections being between about 15% and about 40% of the mean diameter of the pores. In some embodiments, each pore is connected to between about 4 and 12 other pores, such as about 4 to 7 other pores. At least 90% of the pores are connected this way, preferably at least 95% and more preferably at least 97%.

The porous biocompatible material may have a thickness of between about 100 µm and about 1000 µm, such as between about 100 µm and about 500 µm. For the present drain device the thickness of the biocompatible material is chosen in accordance with the desired aqueous humour flow and mechanical strength requirements. Most often the total thickness of the porous section will be between about 200 µm and about 500 µm. This may be obtained by additively combining the respective thicknesses of multiple layers as in the sandwich construction previously referred to.

The porous biocompatible scaffold material may comprise any biocompatible polymer, such as synthetic polymers, naturally-occurring polymers, or mixtures thereof. Exemplary synthetic biocompatible polymers include, but are not limited to, poly(2-hydroxyethyl methacrylate), silicone rubber, poly(ε-caprolactone) dimethylacrylate, polysulphone, poly(methyl methacrylate) (PMMA), fluoropolymers (such as Teflon), polyethylene tetraphthalate (PET or Dacron), polyamide (such as Nylon), polyvinyl alcohol, polyurethane, interpenetrating network polymers, and mixtures thereof. Exemplary naturally-occurring biocompatible polymers include, but are not limited to, fibrous or globular proteins, complex carbohydrates, glycosaminoglycans, or mixtures thereof. Thus, the polymer scaffold may include collages of all types, elastin, hyaluronic acid, alginic acid, desmin, versican, matricelluar proteins such as SPARC (osteonectin), osteopontin, thrombospondin 1 and 2, fibrin, fibronectin, vitronectin, albumin, etc. Natural polymers may be used as the scaffold or as an additive to improve the biocompatibility of a synthetic polymer.

The porous biocompatible material scaffold may be a hydrogel, for example, a degradable hydrogel, which is formed by reacting low-molecular-weight poly(ε-caprolactone) diol with an excess of methacryloyl chloride to give a polyester compound with methacrylate endgroups, the polyester compound being copolymerised with 2-hydroxyethyl methacrylate (HEMA) to yield a cross-linked hydrogel with hydrolysable linkages.

The polymer scaffold generally has a low level of microporosity. The term "microporosity" is a measure of the presence of small micropores within the polymer scaffold itself (as opposed to the pores defined by the scaffold). In some embodiments, all or substantially all of the micropores in the polymer scaffold are between about 0.1 µm and about 5 µm, such as between about 0.1 µm and about 3 µm or between about 0.1 µm and about 2 µm. The term "low level of microporosity" means that micropores represent less than 2% of the volume of the polymer scaffold, as measured by measuring the percentage void space in a cross-section through the polymer scaffold.

Biologically active molecules may be introduced into the porous biomaterial by forming the porous biomaterial in the presence of the biologically active molecules, by allowing the biologically active molecules to diffuse into a porous biomaterial, or by otherwise introducing the biologically active molecules into the porous biomaterial.

The biocompatible material can be formed from a template comprising an array of porogens, that is, any structure that can be used to create a template and is removable after the biocompatible polymer scaffold is formed under conditions that do not destroy the polymer scaffold. For example, PMMA or polystyrene beads can be used.

The pores and porogens may be of any suitable shape, for example, spherical, dodecahedrons, pentagonal dodecahedrons and ellipsoids. The pores and porogens have a roundness of at least 0.1, such as at least about 0.3 or at least about 0.7. The term "roundness" being defined as being $$\frac{6V}{\pi D^3}$$

where V is the volume and D is the diameter of the pores and porogens. As an indication, a sphere has a roundness of 1.0.

The porous biocompatible material described in WO-A-2005/032418 is constructed by forming a template of substantially spherical monodisperse porogens, forming the porous biomaterial round the template, and then removing the template to produce the porous biocompatible material.

The template may be formed by packing the porogens in a mould using ultrasonic agitation or any other suitable method of obtaining a closely packed array of porogens. The porogens may be fused by sintering where the sintering time and/or sintering temperature can be used to increase the size and growth rate of the connections. Other methods may be used for fusing the porogens, for example, by partially dissolving them by treatment with a suitable solvent.

Once the template has been created, the biocompatible polymer scaffold is formed around the template. The polymer scaffold may be formed by polymerising a polymer precursor mixture, comprising polymer precursors and suitable cross-linking reagents, around the template. Impregnation of the template with the precursor mixture may be obtained by application of one or more means depending on the mixture viscosity including; capillary wicking, gravity, vacuum, pressure, or centrifuging.

After the biocompatible polymer scaffold has been formed, the template is removed by solvent extraction to produce the porous biomaterial. If PMMA beads are used as the porogens, they may be extracted by multiple immersions a dichloromethane solution or a 9:1 v/v acetone-water solution. Selection of the solvent is made for compatibility with the final porous material.

In one method for constructing porous polymer scaffold sheets a polymer precursor mixture was formed over a template comprising sintered PMMA beads. The beads were added to moulds comprising two outer layers of solid PMMA about 0.12 mm thick, separated by Teflon spacers of the desired final sheet thickness and further reinforced by sandwiching between clamped microscope slides. The beads were packed using ultrasonic agitation and sintered for 18.5 hours at 190° C. to give neck sizes of about 30% of the bead diameter. After sintering the microscope slides were removed and the resulting PMMA template was infiltrated with the polymer precursor mixture comprised of MED-6215 silicone made by Nusil Technologies LLC, freshly mixed in a 10:1 weight ratio as specified by the manufacturer. The templates were placed in centrifuge tubes and covered with the uncured liquid silicone. Centrifuging was then done at about 24,000 g for 1.5 hours to ensure full penetration of the template by the uncured silicone. After removal from the centrifuge the silicone impregnated templates were placed in an oven at 75° C. for 16 hours to complete the silicone curing. Finally, the PMMA template was removed by agitating in dichloromethane (DCM) solvent and then purified by use of fresh DCM in a Soxhlet extraction apparatus.

For the silicone porous material an analysis of residual non cured components present after the above process showed less that 0.1%, much below the manufacturer's specification of 1% for long term medical implantation.

In an alternative method the porous biomaterial is formed from poly(2-hydroxethyl methacrylate) (polyHEMA) hydrogel. To prepare this the precursor components in Table 1 were used in the volume ratios indicated.

TABLE 1

| Component | Volume (ml) |
| --- | --- |
| 2-hydroxethyl methacrylate (HEMA) | 7.0 |
| Ethylene glycol | 2.1 |
| Water | 0.9 |
| Tetraethylene glycol dimethacrylate | 0.31 |
| Type I collagen in 0.02N acetic acid (4 mg/ml) | 0.5 |
| Ammonium persulphate (0.4 g/ml) | 0.7 |
| Sodium metabisulphite | 0.7 |

The mixture was introduced under a pressure of about 2 atmospheres to a PMMA bead template prepared as above, allowed to polymerise for 24 hours and the PMMA was then extracted with 9:1 v/v acetone-water solution to yield cross-linked porous hydrogel sheets of polyHEMA doped with Type I collagen.

Prior to assembly of the templates, the monodispersity of each bead size of the PMMA beads was examined by light microscopy. For each bead size, at least 95% of the beads had a diameter equal to the mean bead diameter +/−20%.

The monodispersity of the necks in the porogen templates was measured from SEM images. For each bead size, at least 95% of the necks were verified to be between 25% and 35% of the mean bead diameter. SEM was also used to determine the structure of the porous biomaterial. Examination of the SEM images revealed that each pore was connected to between 4 and 7 neighbouring pores and the porous materials had a precisely uniform pore structure.

For any of the materials, specific device shapes may be prepared from the sheets prepared as above by using formed punches or other suitable cutting means.

Figure 1:
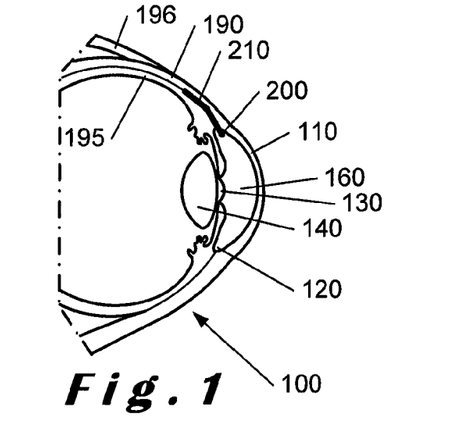
FIG. 1 illustrates a sagittal sectioned view of an eye.
Figure 2:
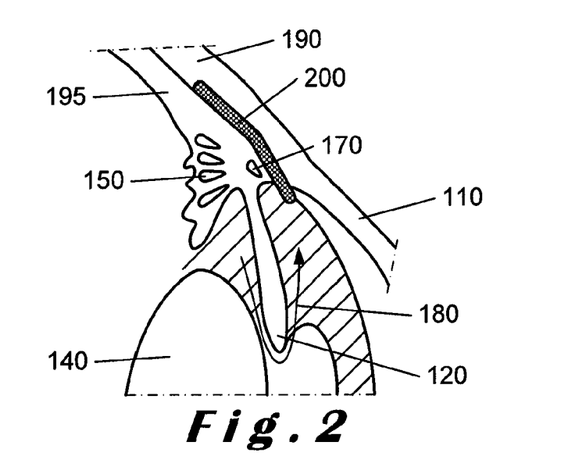
FIG. 2 illustrates an enlarged cross-sectioned view of the eye showing portions of the anterior chamber and outer layers of the eye.

Referring initially to FIGS. 1 and 2, a sagittal section through an eye 100 is shown illustrating the position of the cornea 110, the iris 120, the pupil 130, the lens 140, and the ciliary body 150 (shown more clearly in FIG. 2). The anterior chamber 160 is located between the lens 140 and the cornea 110.

In the normal eye, aqueous humour originates in the ciliary body 150 and circulates between the iris 120 and lens 140 into the anterior chamber 160, and then exits via the porous trabecular meshwork 170 located in the angle between the iris 120 and cornea 110 as indicated by arrow 180. The sclera 190 and the choroid 195 are also shown.

In the glaucomatous eye, meshwork 170 is commonly blocked, causing a damaging pressure increase inside the eye. An integrated IOP sensor and drainage device 200 in accordance with the present invention may be implanted to form a fluid path from the anterior chamber 160 to a sub-scleral area 210, bypassing this blockage and restoring the fluid flow as indicated by arrow 180. With the drainage device thus positioned, the IOP sensor element (not shown) is located so that the pressure in the anterior chamber 160 can be detected, and the antenna element (also not shown) is in the sub-scleral area 210. In this position, pressure data relating to the anterior chamber 160 can be detected by a remote device (not shown) that is coupled to the antenna element. This is described in more detail below.

Figure 3:
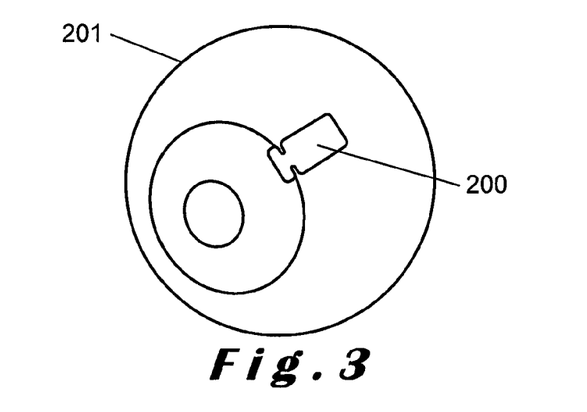
FIG. 3 illustrates a perspective view of the eye showing a preferred location of the device according to the present invention.

In FIG. 3, a preferred supra temporal location for the integrated IOP sensor and drainage device 200 in accordance with the present invention is shown. For a left eye 201, the device 200 is located in a position at between about "1 o'clock" and about "2 o'clock". Similarly, for the right eye, the device 200 is located in a position at between about "10 o'clock" and about "11 o'clock". This provides an anatomical advantage in that the rectus muscles 196 are avoided during surgery and the technical advantage of favourable positioning for wireless communication with an external interrogation device as will be described in more detail below. Moreover, vision is not impaired by the location of the device 200 within the eye. Thus, as used herein, an intended "in use" position includes, for example, any of the positions illustrated in FIGS. 1-3. In general, the device is positioned such that the footplate portion is within the anterior chamber of the eye, and the body portion is within the exterior layers of the eye (FIG. 3).

The integrated IOP sensor and drainage device 200 as described with reference to FIGS. 1 to 3 will be described in more detail in FIGS. 4 to 8 below. Without limitation, the descriptions refer to devices using silicone rubber as the porous biomaterial component. This material has been shown as biologically preferable for long term ocular drainage implants and is well suited to the purposes of this invention.

Figure 4:
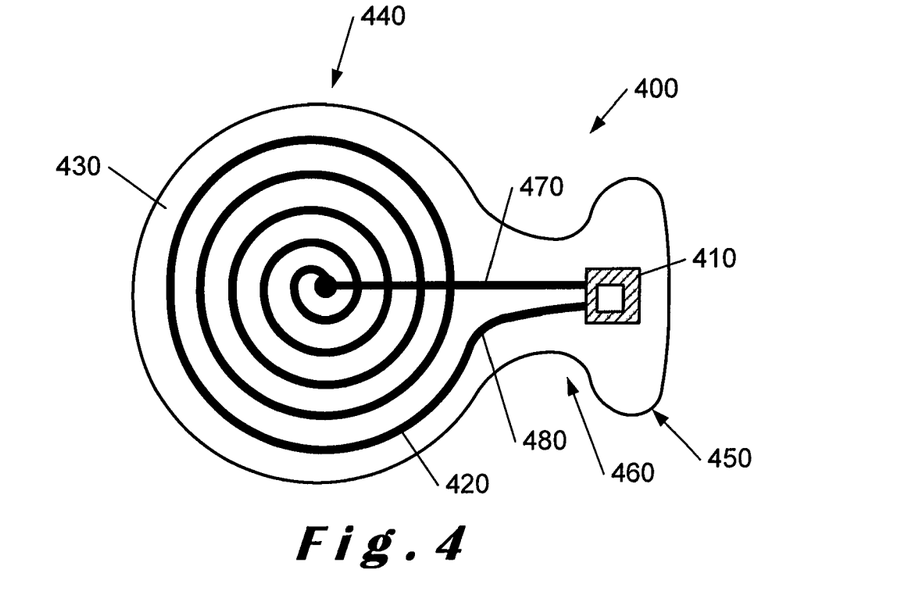
FIGS. 4 and 5 respectively illustrate plan views of first and second embodiments of an integrated IOP sensor and drain device in accordance with the present invention.

In FIG. 4, a plan view of a first embodiment of a combined IOP sensor and glaucoma drainage device 400 in accordance with the present invention is shown. The device 400 comprises an IOP sensor element 410 connected to an antenna element 420 as shown. The IOP sensor element 410 also includes a signal processor (not shown) as will be described in more detail below. The IOP sensor element 410 and the antenna element 420 are located between layers of a porous biocompatible material 430, for example, the porous biocompatible material as described above. This is described in more detail with reference to FIGS. 6 to 8 below. The biocompatible material 430 defines the overall shape of the device 400. In this embodiment, the antenna element 420 is shown as having a substantially circular profile.

Leads 470, 480 are provided for connecting the IOP sensor element 410 with the antenna element 420 as shown. As shown, the leads 470, 480 pass from the footplate portion 450 to the body portion 440 through the neck portion 460.

As shown, the device 400 comprises a substantially circular body portion 440, a footplate portion 450 and a neck portion 460 that connects the body portion 440 to the footplate portion 450. As shown, the antenna element 420 is housed in the body portion 440 and the IOP sensor element 410 is housed in the footplate portion 450. The neck portion 460 provides an anchorage point for the device 400 when it is inserted into an eye as will be described in more detail below.

Typically, the approximate dimensions of the device 400 are given in Table 2 below.

TABLE 2

| Device element | Size (mm) |
| --- | --- |
| Overall length | 11 to 13 |
| Diameter of circular body portion | 8 to 10 |
| Width of footplate portion | 5 |
| Width of neck portion | 3 |
| Thickness of porous section | 0.2 to 0.5 |
| Diameter of pores | 25 μm to 30 μm |

The porous section thickness listed in Table 2 is that available for aqueous humour flow. It may be provided in one or more layers. To further reduce fibrotic reactions to the implant, the porous sections may have an irregular surface comprising a "peaks and valleys" topography contacting the tissue, where the surface variations are often about 100 μm to about 300 μm about the mean thickness of the porous section.

It will be appreciated that the dimensions given in Table 3 may vary in accordance with the particular device 400, and the values given are by way of example.

Figure 5:
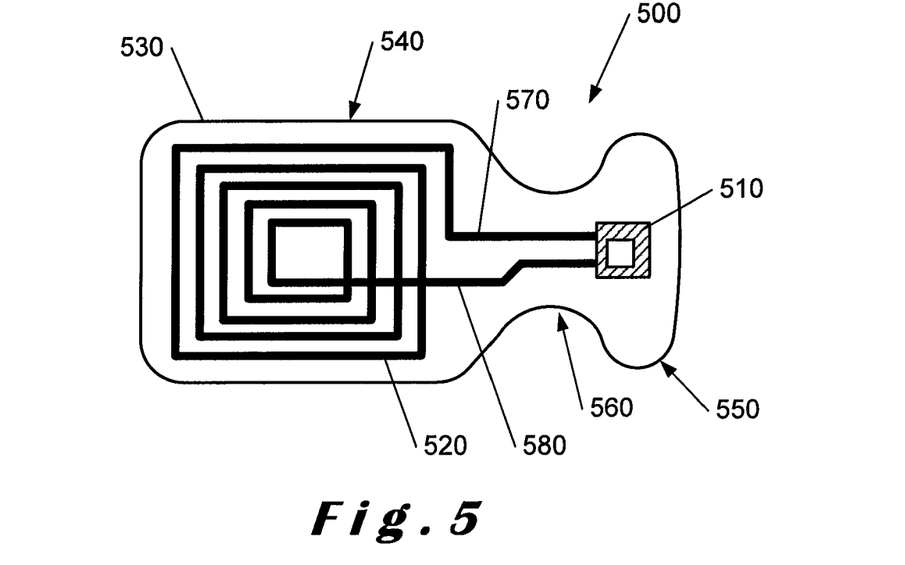

In FIG. 5, a plan view of a second embodiment of a combined IOP sensor and glaucoma drainage device 500 is shown. The device 500 comprises an IOP sensor element 510 connected to an antenna element 520 as shown. The IOP sensor element 510 also includes a signal processor (not shown) as will be described in more detail below. The IOP sensor element 510 and the antenna element 520 are located between layers of the porous biocompatible material 530 as described above. This is described in more detail with reference to FIGS. 6 to 8 below. The biocompatible material 530 defines the overall shape of the device 500. In this embodiment, the antenna element 520 is shown as having a substantially rectangular profile.

Leads 570, 580 are provided for connecting the IOP sensor element 510 with the antenna element 520 as shown. As shown, the leads 570, 580 pass from the footplate portion 550 to the body portion 540 through the neck portion 560.

As shown, the device 500 comprises a substantially rectangular body portion 540, a footplate portion 550 and a neck portion 560 that connects the body portion 540 to the footplate portion 550. As shown, the antenna element 520 is housed in the body portion 540 and the IOP sensor element 510 is housed in the footplate portion 550. The neck portion 560 provides an anchorage point for the device 500 when it is inserted into an eye as will be described in more detail below.

Typically, the approximate dimensions of the device 500 are given in Table 3 below.

TABLE 3

| Device element | Size (mm) |
| --- | --- |
| Overall length | 11 |
| Width of rectangular body portion | 6 |
| Width of footplate portion | 5 |
| Width of neck portion | 3 |
| Thickness of porous section | 0.2 to 0.5 |
| Diameter of Pores | 25 μm to 30 μm |

The thickness of the porous section and the provision of an irregular surface is to be understood in the same manner as for Table 2.

Figure 6:
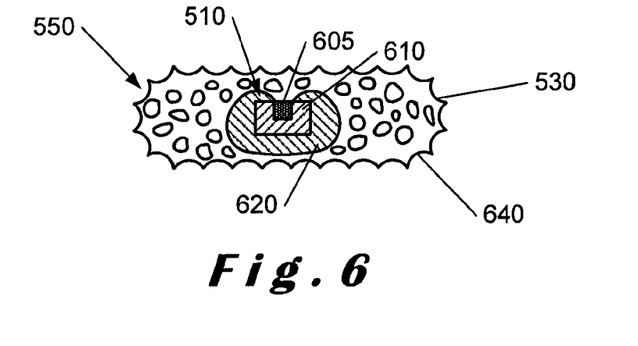
FIG. 6 illustrates a transverse cross-section through the footplate portion of the device shown in FIG. 5.
Figure 7:
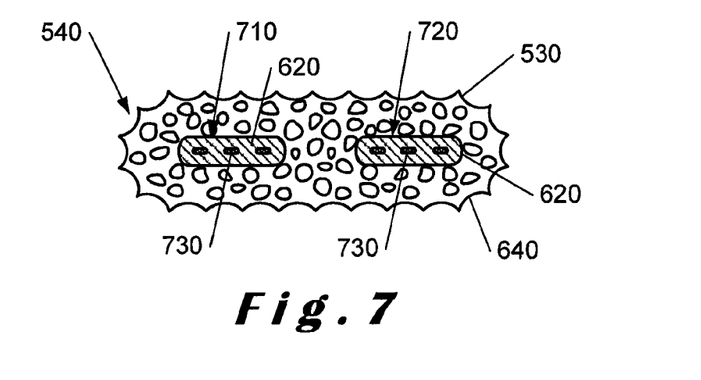
FIG. 7 illustrates a transverse cross-section through the body portion of the device as shown in FIG. 5.
Figure 8:
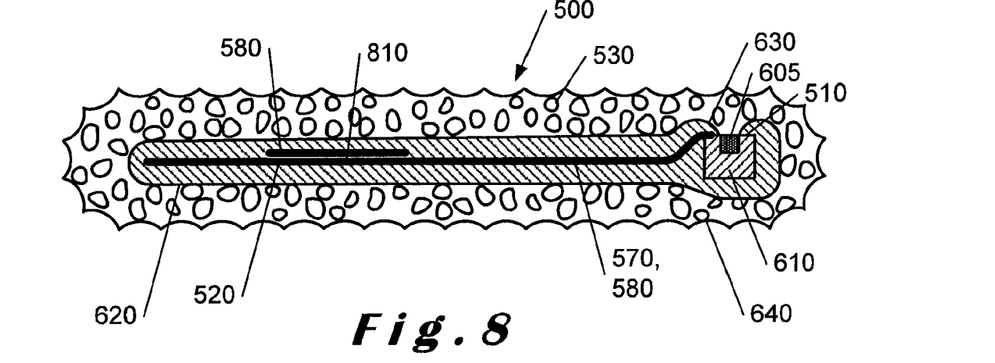
FIG. 8 illustrates a longitudinal cross-section through the device of FIG. 5.

It will be appreciated that the dimensions given in Table 3 may vary in accordance with the particular device 500, and the values given are by way of example. With the dimensions given, resistance of these devices to flow into the footplate area, through the neck and then exiting from the body has been measured as between 0.6 and 0.3 mmHg pressure drop at a flow rate of 1 μl/min, thus allowing alternative sensor locations as referred to above. In FIGS. 6 to 8, sectional views through the device 500 are shown. Elements of the device 500 that have been described above with reference to FIG. 5 have the same reference numerals.

FIG. 6 illustrates a transverse sectioned view of the device 500 taken through the footplate portion 550. This indicates more clearly the internal structure of the footplate portion 550. The IOP sensor element 510 is shown. Here, the IOP sensor element 510 comprises a sensor 605 together with a signal transceiver 610. The sensor 605 and the signal transceiver 610 are embedded in an impermeable protective material 620 having an opening 630 that is located over the IOP sensor element 510. The opening 630 allows fluid communication between the aqueous humour in the anterior chamber of the eye, through the porous biocompatible material 530, when the device 500 is implanted, and the sensor 605.

The sensor 605 and the signal transceiver 610 are substantially contained within the footplate portion 550, and are substantially surrounded by the porous biocompatible material 530. An outer surface 640 of the porous biocompatible material 530 is also shown. The surface 640 comprises open pores of the biocompatible material, the pores having openings as described above, which connect to interior pores within the porous biocompatible material 530.

The sensor 605 is responsive to pressure within the eye. Using the exemplary dimensions for the device 500 given above, pressure differences from the anterior chamber of the eye through the pores in the biocompatible material 530 to the IOP sensor element 510 are negligible and an accurate IOP reading may be obtained.

The exposed face of the IOP sensor element 510 may be protected from direct contact with the aqueous humour in the eye using metallisation with a biologically inert material, for example, titanium. In addition, further sensor elements may be provided (not shown) that operate to provide output signals indicative of one or more of temperature, salinity, glucose level or drug concentration in the aqueous humour.

In one preferred embodiment of the present invention, the same biocompatible material used to form the porous shape 530 that defines the device 500 may also be used in a solid form as part of the impermeable protective layer 620. This is advantageous in practical fabrication of the device and reduces the number of diverse substances introduced into the eye.

In FIG. 7, a transverse sectioned view through the body portion 540 is shown. Here, portions 710, 720 of the antenna element 520 are shown embedded within the impermeable protective layer 620, the same protective layer 620 encapsulating the IOP sensor element 510 and associated signal transceiver 610 as well as the leads 570, 580 and antenna element 520. Whilst the same protective layer 620 may be used to encapsulate the IOP sensor element 510, the leads 570, 580 and the antenna element 520, it is appreciated that each of these components may be encapsulated in separate protective layers (not shown). For example, the leads 570, 580 and the antenna element may be encapsulated in a highly flexible protective layer with the IOP sensor element 510 being encapsulated in another protective layer. It is also envisaged that the leads 570, 580 may also be in a separate protective layer provided they can still provide their function of connecting the IOP sensor element 510 with the antenna 520. Where lead 580 crosses over sections of antenna 520 the conductors are electrically separated by an insulating layer 810 as shown in FIG. 8. This insulating layer 810 may be formed as part of 620 or by other insulating means, for example, a parylene coating.

Portions 710, 720 correspond to an inductive loop (not shown) of conductor elements 730 embedded within the impermeable protective material layer 620. Outer ends of the loop are electrically continuous with leads 570, 580. For most efficient power transfer and data communication performance, antenna element 520 is preferably arranged to enclose the largest practicable area within the boundaries of the body portion 540. It will be appreciated that although the antenna element 520 is described as a spiral, other configurations may be used, for example, a plurality of concentric loops connected together at their outer ends to leads 570, 580 as described above. The spiral, shown for clarity as occupying most of the face area of 540, may advantageously be more tightly confined to the outer perimeter.

Leads 570, 580 and antenna element 520 are may be formed by highly flexible conductors of gold encased in the porous biocompatible material forming the protective layer 620. Such conductors may be made using known electronic assembly techniques, for example, as described by W S Wang and A Salleo, in an article entitled "Flexible Electronics: Materials and applications", Springer, 2009.

The required degree of flexibility of these conductors is determined in accordance with minimizing the force exerted on the implant to conform to the curvature of the sclera surface of the eye. With the dimensions in Table 3, to match the human eye curvature the body area containing the antenna must deflect about 0.7 mm over its length. Using the specific silicone rubber identified in the first method example above, the porous material prepared from this has a measured tensile modulus of 250 kPa, or about 9% that of the solid form. Application of standard plate deflection formulae show that deflection of the device body portion by 0.7 mm results in a tissue reaction pressure of less than 100 Pa due to the porous section using a representative thickness of 0.3 mm. To minimise tissue stress, the composite of porous material and antenna should not increase this by a factor of more than 5 and preferably by not more than 2 times.

By way of comparison the non porous silicone drainage tube used in the Molteno device has a diameter of 0.64 mm and when similarly conformed to the eye curvature, pressure exerted on the surrounding tissue is about 15 times that with the porous drain.

In FIG. 8, a longitudinal sectioned view of the device 500 is shown. Here, the IOP sensor element 510, the antenna element 520 and leads 570, 580 can be seen encapsulated within the impermeable protective material layer 620. The opening 630 is shown within the porous biocompatible material 530. Outer surface 640 of the material 530 is also shown.

Whilst FIGS. 6 to 8 refer to the integrated IOP sensor and drainage device 500 shown in FIG. 5, it will be appreciated that the construction of the IOP sensor and drainage device 400 shown in FIG. 4 will be substantially the same. In all cases the cross-section of the devices 400 and 500, after allowing for the space occupied by the impermeable encapsulation 620, will provide drainage areas 530 substantially equivalent to those in Tables 2 and 3.

In the embodiments shown in FIGS. 4 to 8, the footplate portion 450, 550 is shaped for placement within the anterior chamber of the eye. The neck portion 460, 560 is placed through a surgical incision formed below the sclera into the anterior chamber. Body portion 440, 540 is surgically placed between the sclera 190 and choroid 195 as described with reference to FIGS. 1 to 3 above. Once implanted in the eye, aqueous humour flows in a controlled manner from the anterior chamber through the open pores in the porous biocompatible material 430, 530 that defines the footplate portion 450, 550, the neck portion 460, 560 and the body portion 440, 540 and into the space between the sclera 190 and the choroid 195 (FIGS. 1 and 2) where it is absorbed in the choroidal bed (not shown) and returned to the circulation.

Both the integrated IOP sensor and drainage devices 400, 500 as shown in FIGS. 4 to 8 may be constructed using the following steps. These apply most specifically to the porous material 530 formed from a silicone rubber material approved for long term implantation, such as, MED-6215 made by Nusil Technologies LLC. Variations may be made to use other compositions as listed previously.

1. Construct the entire IOP sensor element/antenna element assembly.
2. Test the assembly before encapsulating it in the impermeable protective material layer 620. In the encapsulating process, the opening 630 is formed over the IOP sensor element 510.
3. With the opening 630 masked, apply a layer of uncured silicone rubber to a controlled thickness, as an adhesion layer, over the encapsulated assembly.

4. Apply sheets of the porous biocompatible material to the uncured ("wet") silicone rubber adhesion layer, forming a sandwich structure with the IOP sensor element/antenna element assembly between at least two sheets of the porous biocompatible material. The adhesion layer thickness controls the degree to which the wet layer will penetrate ("wick") into the pores of the biocompatible material 530. Sheet thickness of biocompatible material can be set to provide the needed cross-section of drain passages after wicking occurs into a controlled depth of pores.

5. Cure the adhesion layer. This bonds the IOP sensor element/antenna element assembly into the biocompatible material that forms the drain for the integrated IOP sensor and drainage device in accordance with the present invention.

The above construction method can be varied to use primers if the impermeable protective layer 620 is formed from a material other than silicone rubber. The use of primers ensures that adequate bonding between the protective layer and the biocompatible material is provided.

All the additional adhesion compositions, primers etc. are specifically identifiable and well known for use in long-term medical implants.

The outer portions of the porous biocompatible material in the sandwich need not be connected to one another in the areas that are not adhered to the IOP sensor element/antenna element assembly. Since the aqueous humour flow is principally longitudinal through the drain (i.e. from 450 through 460 to 440) only the porous path in this direction has to be substantially connected throughout. and maintain a flow section as described above. Thus, without detriment to the drain function, to maintain mechanical integrity and ease of surgical handling, spots of adhesive may be applied to bond ("spot weld") the outer layers of the porous biocompatible material in areas outside a footprint defined by the IOP sensor element/antenna element assembly.

By having the inductive antenna element in the body portion and separate from the sensor in the footplate portion, it avoids the need for having to position both the sensor element and the antenna element within the anterior chamber. In the present invention, as described above with reference to FIGS. 1 to 3, only the sensor element needs to be within the anterior chamber. It will also be appreciated that while the sensor and antenna are shown for convenience as largely symmetrically disposed within the devices, they may be located in various asymmetric arrangements without impairment to function.

This integrated device also provides the advantage that the IOP measurements are independent of the ocular surface and cornea rigidity. In addition, the accuracy of the IOP measurements is not affected by other procedures that may need to be carried out on the eye, for example, keratoplasty or keratoprosthesis.

Figure 9:
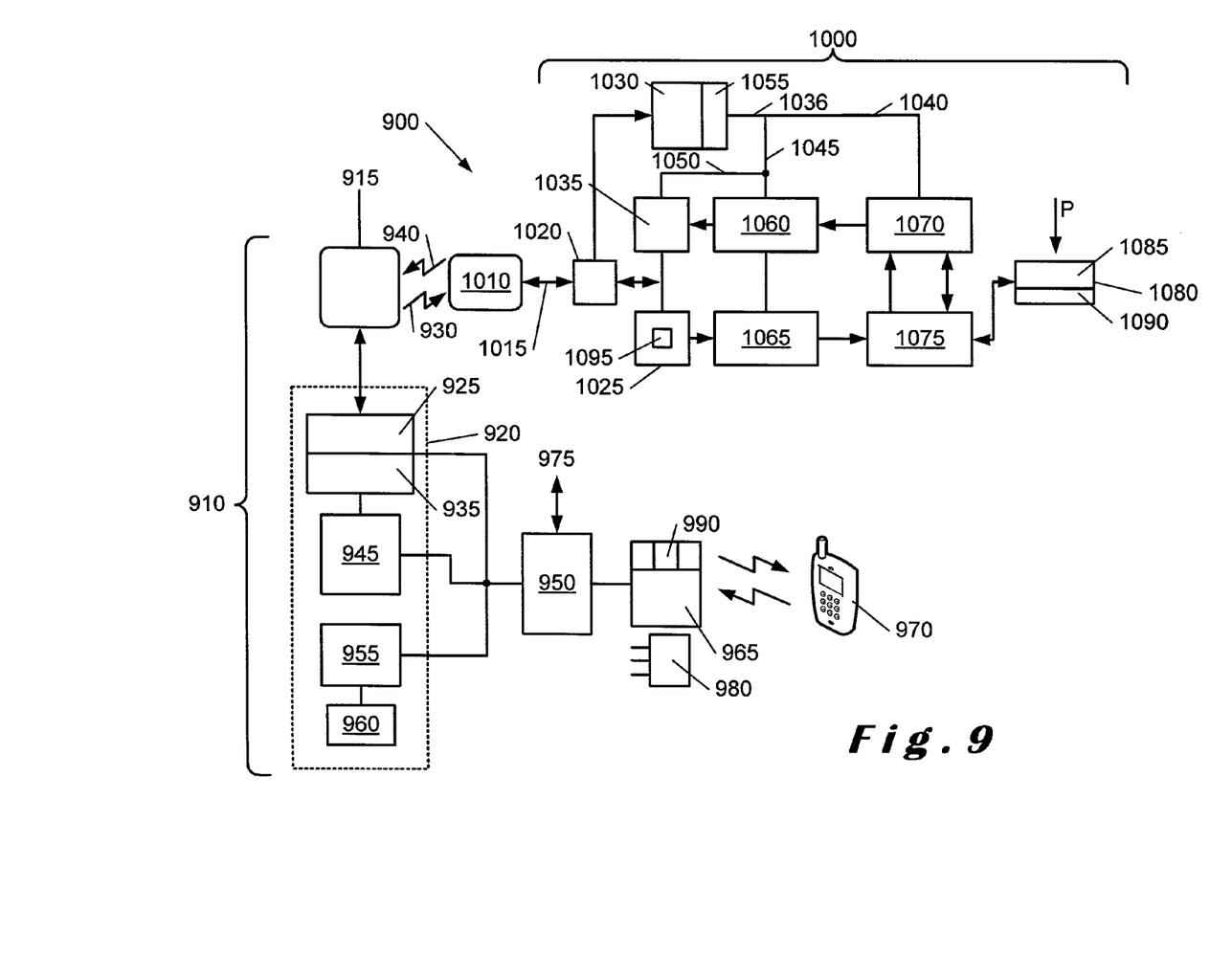
FIG. 9 illustrates a block diagram of a processing system for use with the device as shown in FIGS. 4 to 8 above.

FIG. 9 illustrates a block diagram of an IOP monitoring system 900 in accordance with the present invention. The system 900 comprises a sensor/processor system 1000 that is located within the integrated IOP sensor and drainage device in accordance with the present invention.

The monitoring system 900 also comprises an external processor or external interrogation system 910 that comprises an active interrogation system for the sensor/processor system 1000. The system 910 comprises an inductive antenna element 915 that is powered by a transmitter/receiver assembly 920. The transmitter/receiver module 920 comprises a transmitter circuit 925 that is adapted to provide sufficient power levels to the inductive antenna element 915 for onward transmission, as transmission signal 930, to inductive antenna element 1010 in the sensor/processor system 1000 as will be described in more detail below. It will be appreciated that inductive antenna element 1010 is equivalent to antenna element 420 in FIG. 4 and antenna element 520 in FIGS. 5 to 8 described above.

Transmission signal 930 comprises, first, a burst of energy at a selected frequency, the power level and total delivered energy being sufficient when received via the inductive antenna element 1010 in the sensor/processor system 1000 to activate the latter. Secondly, transmission signal 930 is preferably coded to specifically address a sensor/processor system 1000 with which it is associated so as to only allow activation of the system 1000 on receipt of the correct code. Failure to build in this coding capability would allow unwanted activation of the sensor/processor system 1000 by stray signals and other risk situations. This differs from radio frequency identification (RFID) system where all tags in range are required to respond. It will be appreciated that more than one sensor/processor system 1000 may be interrogated by one external interrogation system 910 provided each system 1000 is interrogated with its unique code. This applies particularly to patients with bilateral glaucoma implants and may also be used in a further aspect to provide a physician "master key" access capability.

In addition to the transmitter 925, the transmitter/receiver module 920 comprises a receiver 935, which is adapted to filter and decode signals 940 transmitted by the inductive antenna element in the sensor/processor system 1000 as will be described in more detail below, a buffer 945 connected to the receiver 935 and to a microprocessor 950. The buffer 945 receives measurements transmitted from the sensor/processor system 1000 and interfaces with the microprocessor 950.

The transmitter/receiver module 920 also optionally includes an ambient condition sensor and interface 955 that may be used to sense ambient atmospheric pressure and temperature for applying corrections, if required, to the original measurements received by the receiver 935 so as to obtain a valid medically recorded IOP value. In additional, sensor 955 may also receive signals from a physiological monitor 960 that include, without limitation, pulse rate and respiration.

As shown, the transmitter 925, the receiver 935, the buffer 945 and the sensor 955 are connected to the microprocessor 950. The microprocessor 950 operates to provide:

a) sequence control for transmitter/receiver module 920;

b) interface and receipt of IOP data from the buffer 945;

c) receipt and application of ambient, physiological conditions from the sensor 955;

d) programmed calculation of the medical record IOP reading from each sequence of measurements;

e) a wireless interface 965 adapted for communication with a cell phone 970 or other similar device;

f) an external interface means 975 such as that provided by the universal serial bus (USB) for data download and for setting of the operating conditions for the device by a physician or other medically trained person; and g) management of power consumption from battery 980.

Well known means, for example, "Bluetooth" (registered trademark of the Bluetooth Special Interest Group) may be used for the wireless interface 965 with the cell phone 970. Use of a programmed applications package in the cell phone 970 provides for convenient patient information display, alarms and physician contact and data transmission for the patient.

During the programmed calculation of the medical record IOP reading, the microprocessor 950:

i) detects and rejects corrupted data;

ii) reduces noise by averaging readings over the received signals;

iii) monitors and retains IOP trends, updating data relating to each patient within the monitoring system 900 with each successive record;

iv) maintaining a local indication of the IOP record and trend on a display 990; and v) indicates to the patient by audible or other alarm means (not shown) excessively high or low IOP values.

The external interrogation system 910 also includes a charger (not shown) for providing power to the battery 980. However, external power for charging is most conveniently provided via the USB interface 975.

Turning now to the sensor/processor system 1000, it comprises an inductive antenna element 1010 that interfaces with the inductive antenna element 915 of the external interrogation system 910. The antenna element 1010 is connected via leads 1015 to a transceiver protection switch 1020. The transceiver protection switch 1020 is connected to a decoder 1025, a detector 1030 and a transmitter 1035.

Antenna element 1010 corresponds to antenna elements 420, 520 as described above with respect to FIGS. 4 and 5. Leads 1015 correspond to leads 470, 480 (FIG. 4) and leads 570, 580 (FIG. 5).

Detector 1030 converts the received signal to direct current at a voltage and current level adapted to the operating power requirements of electronics within the integrated IOP sensor and drainage device in accordance with the present invention. The power is then distributed to other processing elements within the sensor/processor module 1000 via connections 1036, 1040, 1045, 1050 as shown. An energy storage element 1055, preferably a capacitor, may be added to stabilise the power supply from the detector 1030, provide short term power for readout signals from 1000 and to provide a buffer against fluctuations in the signal 930 transmitted from the external interrogation system 910 as received by the inductive antenna element 1010. Fluctuations may occur, for example, due to changes in the relative positions of inductive antenna elements 1010 and 915 due to patient motion.

Transceiver protection switch 1020 preferably provides:

a) filtering to attenuate signals received from sources other than external interrogation system 910;

b) means for overload protection to prevent implant damage from strong interfering signals, for example, such as from patient use of a cellular telephone; and c) switching and protection of the detector 1030 and the decoder 1025 from data readout transmissions from transmitter 1035.

The sensor/processor system 1000 also includes an encoder 1060, a transmitter control module 1065, an analogue-to-digital converter (ADC) 1070, a sensor interface 1075 and a sensor assembly 1080. The sensor assembly 1080 includes an IOP sensor 1085 and a pressure reference 1090. Assembly 1080 corresponds to the sensor identified as 605 in FIGS. 6 and 8.

The operation of the monitoring system 900 will now be described in more detail.

A transmit signal 930 transmitted by the inductive antenna element 915 of the external interrogating device 910 is received at the inductive antenna element 1010 and is passed to the transceiver protection switch 1020 via leads 1015. The transceiver protection switch 1020 passes the signal to the detector 1030 for conversion into power as described above, and to the decoder 1025. Decoder 1025 comprises means to extract the received address code and compare this with an internally stored template contained in a non volatile memory (NVM) 1095. On detecting a code match, decoder 1025 then provides timing and activation commands to enable sensor readings to be taken from the sensor assembly 1080 and transmitted to the external interrogation device 910.

Decoder 1025 passes an activation signal to the transmitter control module 1065 which, in turn, passes a signal to the sensor interface 1075 to the ADC 1070 and to the sensor assembly 1080. It will be apparent that further capabilities, for example, multiple code templates, can be provided in the NVM 1095, allowing unique codes for each patient device/external interrogation system combination, as well as a distinct code for medical access.

More explicitly, decoder 1025 provides commands to sensor interface 1075 and later in the interrogation cycle to transmitter control module 1065. When activated, sensor interface 1075 powers sensor 1080 and buffers the resultant analogue signal representing a pressure reading.

Sensor element 1080 comprises a pressure-sensitive component 1085, and a reference-pressure component 1090. Without alteration of the intended function, pressure-sensitive component 1085 uses a microelectromechanical sensor (MEMS) element that deflects when pressure is applied to a surface (not shown). In one embodiment, the MEMS element forms one plate of a capacitor formed on a silicon substrate. In a further embodiment, piezo-resistive components that are sensitive to pressure changes may be arranged on the deflectable element. In a still further embodiment, piezoelectric components such as those formed from polyvinylidene fluoride (PVDF) may be used.

Pressure-reference component 1090 comprises a sealed cavity (not shown) where one wall is formed by the pressure-sensitive component 1085 and the other walls are formed by substantially rigid portions of the sensor 1080. The cavity may be evacuated to form an absolute pressure sensor, or, preferably, may be pre-pressurised to a predetermined reference pressure, for example, standard atmospheric pressure.

The output signal from the sensor 1080, representing IOP, is buffered and most often amplified by the sensor interface 1075 before being applied to ADC 1070. The ADC 1070 converts the analogue signals to digital signals, provides an electrical reference for the conversion, and also provides a temporary storage for the resultant IOP value. In some sensor embodiments, the ADC 1070 may also compensate for offsets or non-linearity in the output signal from the sensor 1080, for example, using a look-up table that is implemented at manufacture.

In one embodiment, each medically recorded IOP value is determined from multiple readings taken at a rate from between about 3/s to about 20/s over a time interval between about 10 s to about 60 s to allow averaging across IOP pulsations that may be caused by the patient's blinking, respiration or vascular pulsations. This timing protocol is preferably achieved by pulsing or other modulation of transmission signal 930, thus allowing the protocol to be readily varied to suit individual patients, while minimising the internal complexity of the assembly 1000. Additionally, the intervals between each record may be determined by external interrogation system 910.

Encoder module 1060 encodes the IOP values received from the ADC 1070. A suitable encoding method is the conversion of IOP measurements to a binary coding of at least 8 bits, allowing for 256 levels of IOP or a resolution of about 0.2 mmHg over a 5-mmHg to 50-mmHg IOP range. Certain code values may be reserved for indicating predetermined value IOP values outside this range, for example, less than 5 mmHg or greater than 50 mmHg. Naturally, any suitable ranges and values can be set and these ranges and values may be tailored to the requirements of an individual patient in whom the integrated IOP sensor and drainage device is implanted. Each binary code may be attached to a defined header and other identification bit series to form a standard length and format code string suitable for high reliability wireless transmission and reception. Such codes are well known in the RFID field and will not be addressed further here.

Under the control of the transmitter control module 1065, the code string is then used to modulate a transmit signal generated by transmitter readout module 1035. The modulated signal is passed to the transceiver protection switch 1020 and onto inductive antenna element 1010 for transmission as readout signal 940 for the external interrogation system 910, the signal 940 being received by the antenna element 915.

It is preferred that each individual reading of the multiple set described above is transmitted to the external interrogation system 910 in the intervals between the pulses of the transmit signal 930 from the antenna element 915. An exemplary pressure measurement sequence comprises:

a) transmission of a transmit signal 930 from the antenna element 915 to the antenna element 1010, the transmit pulse being under control of external interrogation system 910;

b) reception of the transmit signal by the antenna element 1010;

c) conversion to operating power for the sensor 1080 by the detector 1030 and device activation by address code recognition in the decoder 1025;

d) reading of an IOP measurement from sensor 1080;

e) encoding and transmission of the sensed IOP measurement in electrical form via ADC 1070, encoder 1060, and transceiver protection switch 1020 to antenna element 1010;

f) transmission of the readout signal 940 from the antenna element 1010 to the antenna element 915 in the external interrogation system 910; and g) return to unpowered quiescent state until the next transmit signal 930 is received.

External interrogating system 910 may be physically realised as an attachment to an eyeglass frame that can be worn for long periods of time by a patient in whom the device has been implanted, a hand-held wand placed in the vicinity of the subject eye or other convenient forms. It will be appreciated that the eyeglass frame will allow multiple readings to be taken of the IOP as long as the patient wears the eyeglasses. However, if IOP measurements are needed to be taken at night, when the patient is asleep, a modified eye-patch or sleep mask, incorporating the external interrogating device, may be worn. Alternative means include forming antenna 915 as a pliable sheet used under the patient pillow. To compensate for the increased distance to implant antenna 1010 and for patient movement the area enclosed by 915 when provided in such form may be made much larger than for an eyeglass frame, eye patch, mask or wand location.

In addition, IOP measurements may be transmitted to a remote location, for example, the office of a medical practitioner when the IOP values exceed predetermined threshold values, using cellular telephony or other communications system as is well known. The IOP measurements may also be displayed for the patient's information, for example, on his/her cellular phone.

It will be appreciated that the system 910 comprises the active part complementing the sensing function of the implanted device 200 (FIGS. 1 to 3) as the implant itself has no internal power supply In the absence of 910 or case of a sensing failure in 1000, no chemicals are present in the eye as would be the case with a internal battery and the aqueous drainage function of the integrated implant is unaffected Various modifications may occur to those skilled in the art without departing from the intent and scope of the invention.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An integrated intraocular device comprising:
   an intraocular pressure sensor element;
   an antenna element; and
   an aqueous humour drainage element, wherein, the drainage element consists of a porous biocompatible material, wherein the porous biocompatible material substantially encases the intraocular pressure sensor element and the antenna element, and wherein the porous biocompatible material comprises substantially spherical interconnected open pores having a mean pore diameter between 20 μm and 40 μm and is configured to provide isotropic flow paths for draining aqueous humour into tissue.

2. The integrated intraocular device according to claim 1, wherein the drainage element comprises a body portion housing the antenna element and a footplate portion housing the intraocular pressure sensor element.

3. The integrated intraocular device according to claim 2, wherein the body portion and the footplate portion are connected to one another by a smaller section neck portion for retaining the drainage element within the eye.

4. The integrated intraocular device according to claim 2, wherein the body portion has a periphery and is substantially circular and the antenna element comprises a circular spiral located within the circular body portion.

5. The integrated intraocular device according to claim 4, wherein the antenna element is substantially arranged around the periphery of the body portion.

6. The integrated intraocular device according to claim 2, wherein the body portion is substantially rectangular and the antenna element comprises a rectangular spiral located within the rectangular body portion.

7. The integrated intraocular device according to claim 2, wherein the antenna element and the intraocular pressure sensor element are connected by leads that pass between the body portion and the footplate portion.

8. The integrated intraocular device according to claim 7, further comprising at least one protective layer located between the intraocular pressure sensor element, the antenna element, the leads and the porous biocompatible material, the porous biocompatible material encasing each protective layer.

9. The integrated intraocular device according to claim 8, wherein a single protective layer is formed around the intraocular pressure sensor element, the antenna element and the leads, the single protective layer having an opening near the intraocular pressure sensor element to allow pressure of the aqueous humour to be measured through the porous biocompatible material.

10. The integrated intraocular device according to claim 1, wherein the porous biocompatible material comprises a natural polymer.

11. The integrated intraocular device according to claim 1, wherein the porous biocompatible material comprises a synthetic polymer.

12. The integrated intraocular device according to claim 11, wherein the synthetic polymer comprises silicone rubber.

13. The integrated intraocular device according to claim 1, wherein porous biocompatible material has a mean thickness of between 100 μm and 1000 μm.

14. The integrated intraocular device according to claim 13, wherein the mean thickness of the porous biocompatible material is between 100 μm and 500 μm.

15. The integrated intraocular device according to claim 14, wherein the mean thickness of the porous biocompatible material is between 200 μm and 500 μm.

16. The integrated intraocular device according to claim 1, wherein the mean pore diameter is between 25 μm and 30 μm.

17. The integrated intraocular device according to claim 1, wherein the substantially spherical open pores have pore interconnections having a width of between 15% and 40% of the mean pore diameter.

18. The integrated intraocular device according to claim 1, wherein the porous biocompatible material comprises an irregular outer surface having a topography comprising a plurality of peaks and valleys, each peak having a height of between about 100 μm and about 2000 μm and at least two adjacent peaks define a valley, the valley having a floor from which the heights of the adjacent peaks are measured.

19. The integrated intraocular device according to claim 18, wherein the porous biocompatible material has a mean thickness of between 100 μm and 1000 μm, and wherein the irregular outer surface has surface variations of between 100 μm and 300 μm from the mean thickness of the porous biocompatible material.

20. The integrated intraocular device according to claim 1, wherein the porous biocompatible material provides a drain for aqueous humour flow with a resistance not exceeding 1 mmHg pressure drop for a flow of 1 μl/min.

21. The integrated intraocular device according to claim 1, wherein the antenna element comprises an inductive antenna element.

22. The integrated intraocular device according to claim 21, wherein the antenna element is passive.

23. The integrated intraocular device according to claim 1, wherein the intraocular pressure sensor element is passive.

24. The integrated intraocular device according to claim 1, further comprising an intraocular pressure sensor processing system, the intraocular pressure sensor element forming a part of the intraocular pressure sensor processing system.

25. The integrated intraocular device according to claim 24, wherein the intraocular pressure sensor processing system comprises a decoder for decoding signals received by the antenna element and a detector for obtaining power signals from the signals received by the antenna element.

26. The integrated intraocular device according to claim 25, wherein the intraocular pressure sensor processing system further comprises an energy storage module for storing energy relating to the power signals derived from the received signals.

27. The integrated intraocular device according to claim 24, wherein the intraocular pressure sensor processing system comprises an encoder for encoding signals to be transmitted by the antenna element.

28. An intraocular pressure monitoring system comprising:
   an interrogation and processing system;
   an integrated intraocular device, the intraocular device being arranged to communicate wirelessly with the interrogation and processing system, wherein the integrated intraocular device comprising: an intraocular pressure sensor element; an antenna element; and an aqueous humour drainage element, and wherein, the drainage element consists of a porous biocompatible material, wherein the porous biocompatible material substantially encases the intraocular pressure sensor element and the antenna element, and wherein the porous biocompatible material comprises substantially spherical interconnected open pores having a mean pore diameter between 20 μm and 40 μm and is configured to provide isotropic flow paths for draining aqueous humour into tissue.

29. The intraocular pressure monitoring system according to claim 28, wherein the interrogation and processing system comprises a transceiver element for transmitting activation signals to the integrated intraocular device and for receiving signals corresponding to intraocular pressure measurements taken by the integrated intraocular device when activated.

30. The intraocular pressure monitoring system according to claim 29, wherein the interrogation and processing system comprises a communications module for transmitting data relating to the intraocular pressure measurements to a remote location.

31. The intraocular pressure monitoring system according to claim 28, wherein the interrogation and processing system is mounted in at least one of a pair of eye glasses, a wand, a pillowcase, and a sheet.

32. A method of monitoring intraocular pressure, the method comprising the steps of:
   (a) implanting an integrated intraocular device including:
      (i) an intraocular pressure sensor element;
      (ii) an antenna element; and
      (iii) an aqueous humour drainage element, wherein the drainage element consists of a porous biocompatible material, wherein the porous biocompatible material substantially encases the intraocular pressure sensor element and the antenna element, and wherein the porous biocompatible material comprises substantially spherical interconnected open pores having a mean pore diameter between 20 μm and 40 μm and is configured to provide isotropic flow paths for draining aqueous humour into tissue; and
   (b) determining intraocular pressure measurements using the intraocular pressure sensor element within the integrated intraocular device;
   wherein, step (a) comprises implanting the portion of the device having the intraocular pressure sensor element within the anterior chamber of the eye.

33. The method of monitoring intraocular pressure according to claim 32, wherein the drainage element comprises a body portion housing the antenna element and a footplate portion housing the intraocular pressure sensor element, and the body portion and the footplate portion are connected to one another by a smaller section neck portion for retaining the drainage element within the eye, and wherein step (a) comprises making a limbal incision in the eye; positioning the footplate portion within the anterior chamber of the eye, the neck portion being located in the limbal incision; and positioning the body portion within the exterior layers of the eye.

34. A method of monitoring intraocular pressure according to claim 33, wherein step (a) further comprises positioning the body portion between the choroid and the sclera of the eye.

35. A method of monitoring intraocular pressure according to claim 32, wherein step b) comprises using an extracorporeal device to interface with the intraocular pressure sensor element to obtain an output of the intraocular pressure measurements.

* * * * *